United States Patent [19]
Brown

[11] Patent Number: 5,769,090
[45] Date of Patent: Jun. 23, 1998

[54] FEMALE SECURITY DEVICE

[76] Inventor: Norma Brown, 2721 Kings Hwy., Apt. 4M, Brooklyn, N.Y. 11229

[21] Appl. No.: 915,166

[22] Filed: Aug. 20, 1997

[51] Int. Cl.$^6$ ........................................... A61F 5/37
[52] U.S. Cl. ............................... 128/883; 128/884
[58] Field of Search .................... 128/846, 883, 128/884; 600/38–41

[56] References Cited

U.S. PATENT DOCUMENTS

| | | | |
|---|---|---|---|
| 14,739 | 4/1856 | Sibley | 128/883 |
| 429,068 | 5/1890 | Sommerville | 128/883 |
| 723,259 | 3/1903 | Fraser | 128/883 |
| 789,286 | 5/1905 | Main | 128/883 |
| 826,377 | 7/1906 | Sonn | 128/883 |
| 1,215,028 | 2/1917 | Jones | 128/883 |
| 1,243,629 | 10/1917 | Roddy | 128/883 |
| 1,266,393 | 5/1918 | Bowen | 128/883 |
| 4,016,875 | 4/1977 | Levesque . | |
| 4,030,490 | 6/1977 | Vogel . | |
| 4,167,183 | 9/1979 | Barlow . | |
| 4,237,876 | 12/1980 | Rumph et al. . | |
| 5,353,811 | 10/1994 | Davis et al. . | |

*Primary Examiner*—Michael A. Brown
*Attorney, Agent, or Firm*—Michael I. Kroll

[57] ABSTRACT

A female security device placed within a vaginal cavity to protect and minimize physical damage caused by physical sexual intercourse. The female security device includes a cylindrical housing including a first open end and a second closed end. The second closed end is inserted deeper within the vaginal cavity than the first open end and an inner surface of the cylindrical housing is able to absorb any fluid dispensed therein. Pressure sensors are positioned therearound for sensing contractions in walls of the vaginal cavity and a pressure sensor is positioned therein for sensing pressure caused by insertion of an object into the cylindrical cavity. A needle is positioned to extend into the cylindrical cavity for contacting the object inserted therein and retaining a tissue sample of the object. A microcomputer is connected to the external and internal sensors for determining when an object has been inserted therein and a reservoir is connected for releasing an identification dye to discolor the object upon making such a determination. Furthermore, the needle is able to inject a tissue irritant into the object upon contact therewith and thus cause an irritation to form. An auditory recorder may also be connected to the microcomputer and activated upon a determination that an object has been inserted therein for recording all sounds occurring during the sexual intercourse and a vibrating ring may be activated at that time to notify the user that the device has been activated.

19 Claims, 7 Drawing Sheets

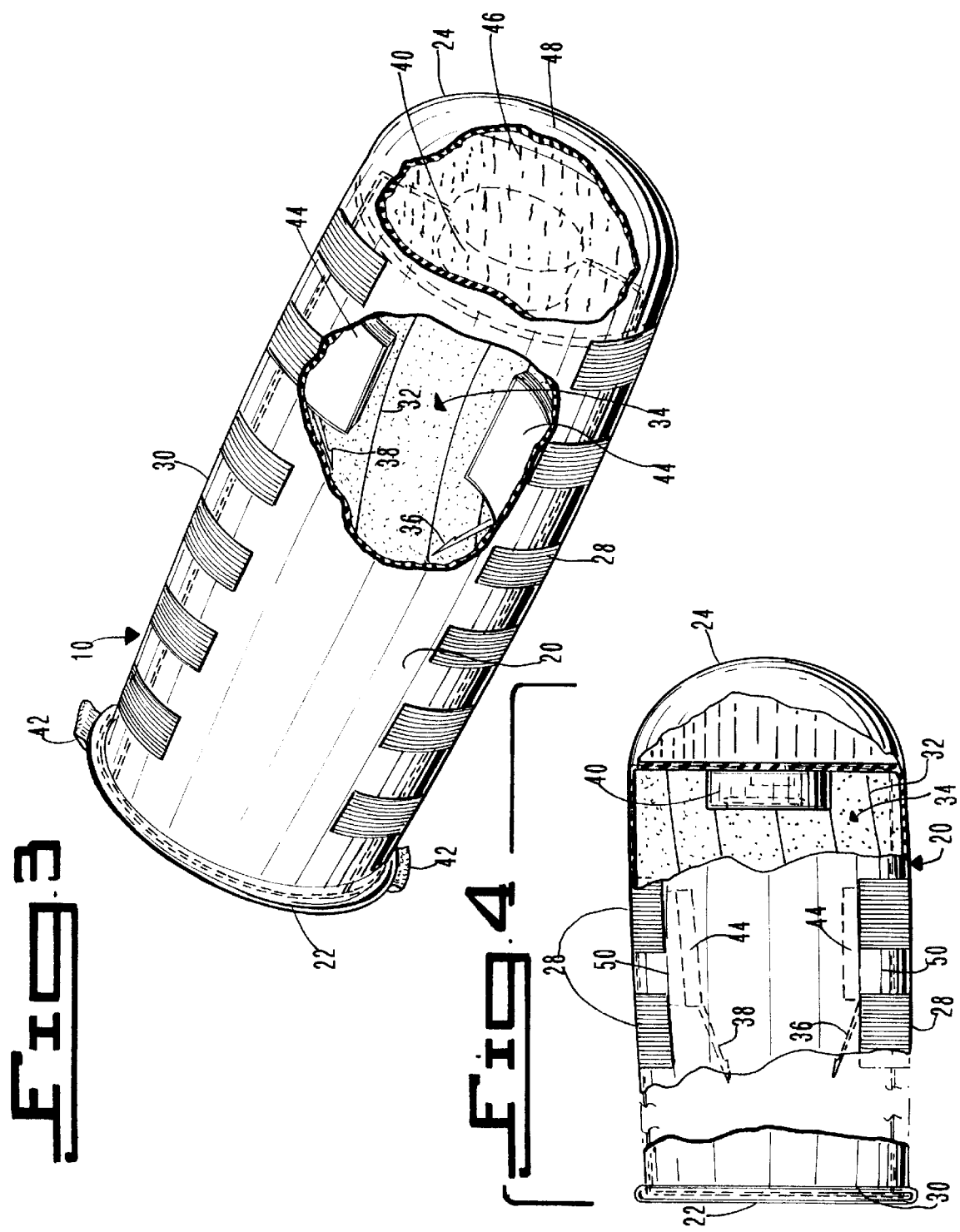

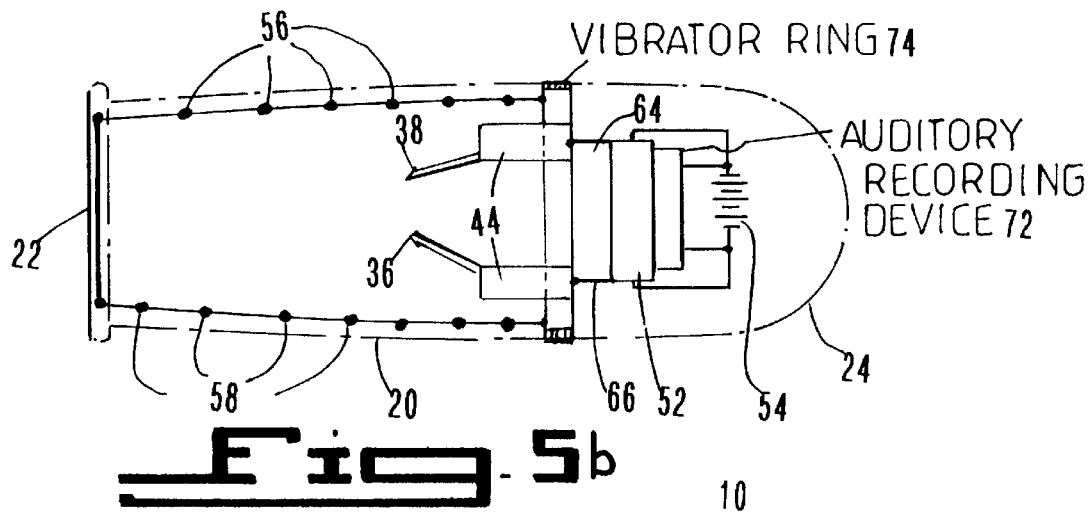
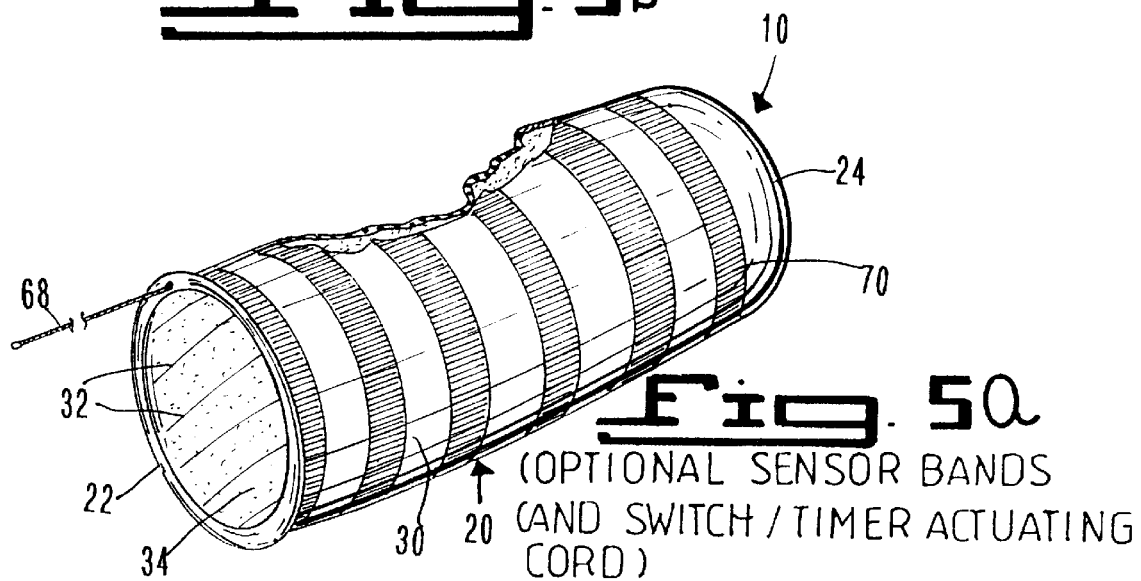
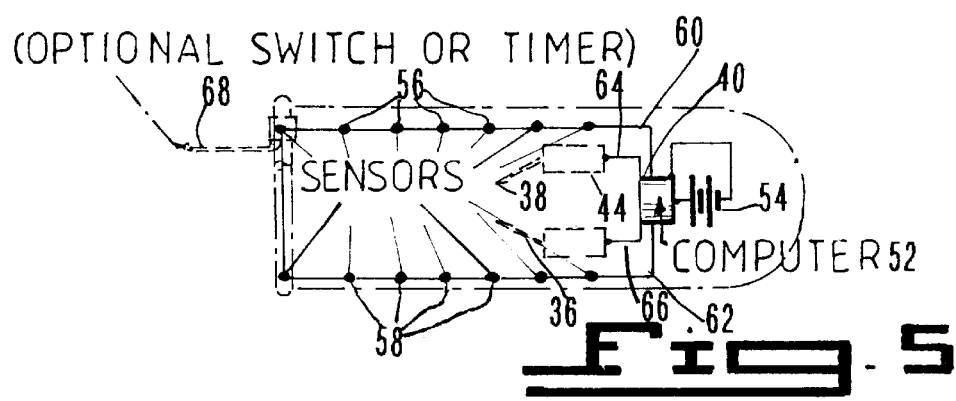

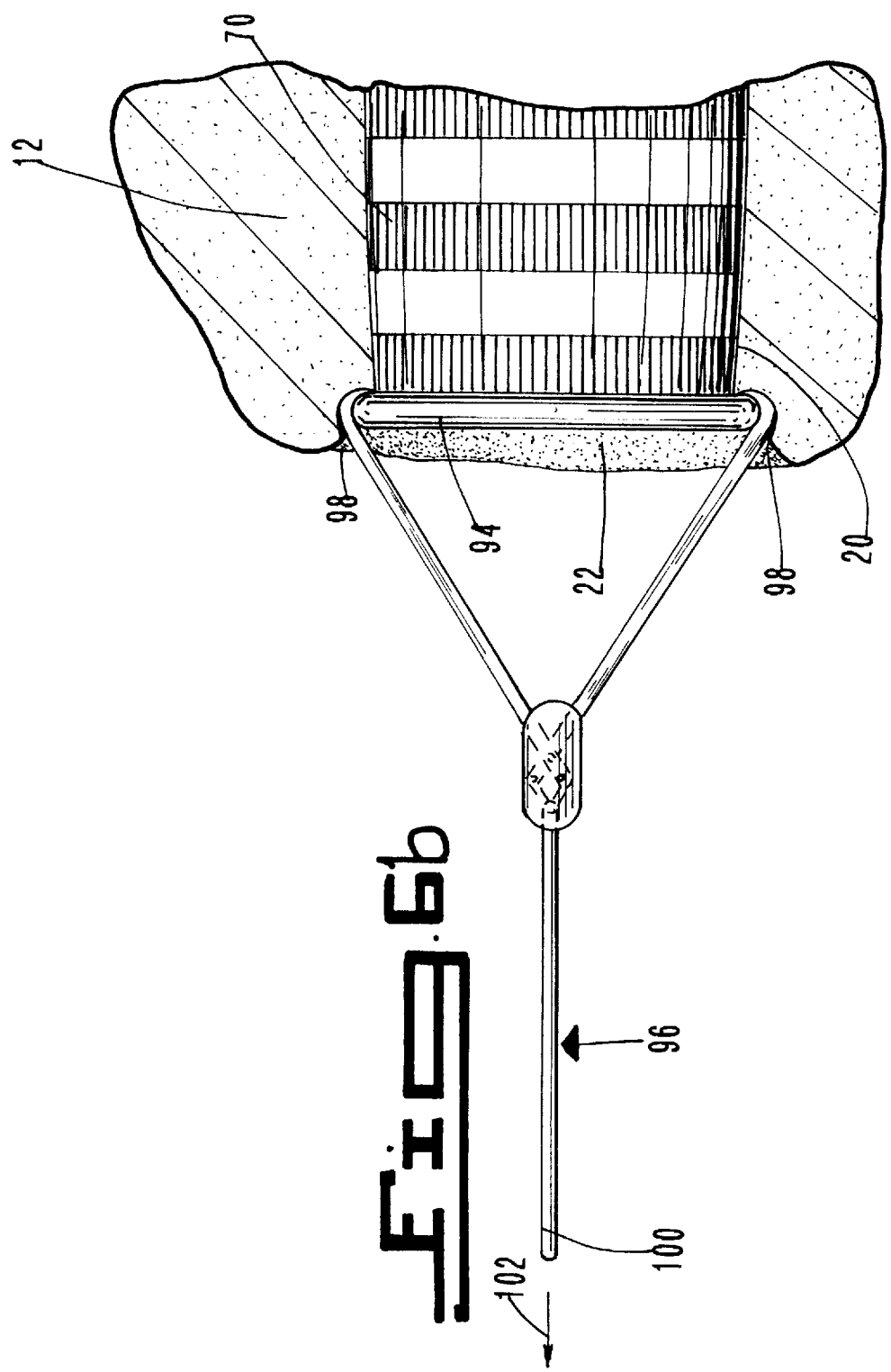

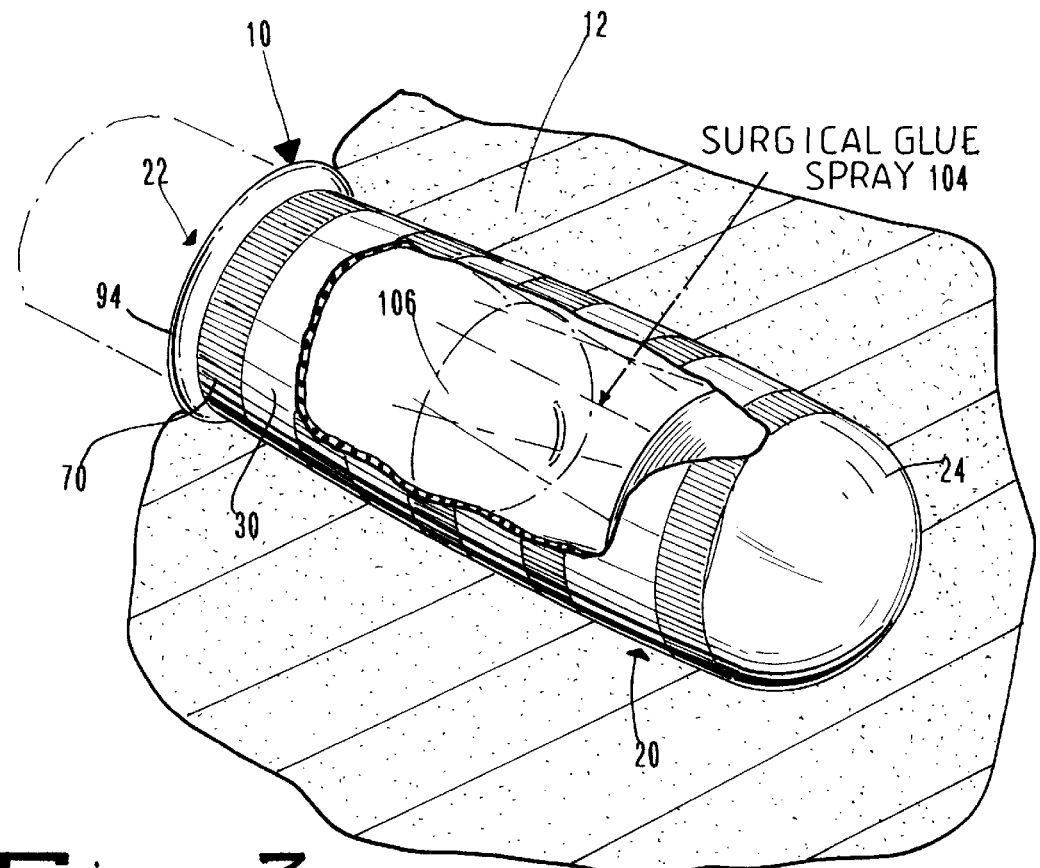
Fig. 7
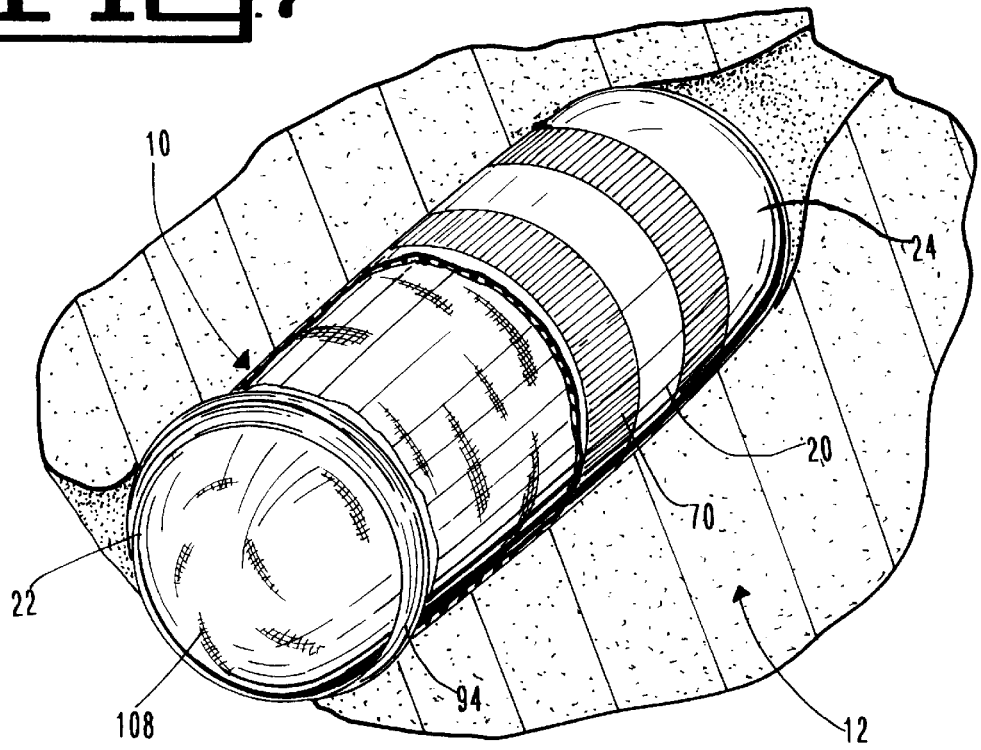
Fig. 8 (AIRBAG DEPLOYED AS BARRIER TO PENETRATION)

FEMALE SECURITY DEVICE

BACKGROUND OF THE INVENTION

1. Field of the Invention

The present invention relates generally to sexual protection devices for females and, more specifically, to a device for defending against and providing protection for females against rape.

2. Description of the Prior Art

Numerous sexual and rape protection devices for females have been provided in the prior art For example, U.S. Pat. Nos. 4,016,875; 4,030,490; 4,167,183; 4,237,876 and 5,353, 811 all are illustrative of such prior art. While these units may be suitable for the particular purpose to which they address, they would not be as suitable for the purposes of the present invention as heretofore described.

U.S. Pat. No. 4,016,875

Inventor: Alston L. Levesque

Issued: Apr. 12, 1977

A plurality of rigid members forming lateral enlargements engage a plurality of housing members having lateral slots to secure the enlargements, springs within the housing press the rigid members distal to the housing to retain the device within a woman's vagina and a blade, which may have barbs on its edge, is pivotally mounted within a slot in the internal surface of the housing.

U.S. Pat. No. 4,030,490

Inventor: George N. Vogel

Issued: Jun. 21, 1977

Female protective device to prevent rape, the device including an elongated slender shaft having a sharp end, a first annular enlargement fixed around the shaft adjacent to but spaced from the sharp end, and a second enlargement connected by a flexible joint to the other end of the shaft. The device is worn internally with the sharp end pointed outwardly.

U.S. Pat. No. 4,167,183

Inventor: Charles Barlow

Issued: Sep. 11, 1979

An anti-rape device adapted to be inserted into the vaginal cavity of a human female, which comprises a base member to which is attached elongated penis penetrating means which projects outwardly toward the mouth of the vaginal cavity when the device is operationally positioned within the vaginal cavity of a human female. The elongated penis penetrating means is surrounded or enveloped by retractable means which serves to prevent the walls of the vaginal cavity from contacting the penis penetrating means and which is adapted to be retracted upon penetration of the vaginal cavity by a male penis to permit penetration of the penis by the penis penetrating means.

U.S. Pat. No. 4,237,876

Inventor: Joel D. Rumph et al.

Issued: Dec. 9, 1980

An anti-rape device having a hollow housing adapted to be worn within a human vagina. The housing has a front opening and contains a hypodermic syringe having a volume of rape-deterring fluid and a needle facing and aligned with the front opening. Actuator means in the housing are provided which include housing means such as a spring to force the needle through the front opening and inject the fluid, cocking means to cock the device into a position which totally shields the needle within the housing, and prevents action of the spring, and trigger means which automatically releases the cocking means, upon forceful penis penetration of a vagina containing the device, to permit the spring to protrude the needle and inject the fluid into the penis. Preferably, the fluid is a quick-acting, safe narcotic such as scopolamine, or the like to render the rapist unconscious.

U.S. Pat. No. 5,353,811

Inventor: Sandra L. Davis et al.

Issued: Oct. 11, 1994

The invention is made of a flexible metal rim containing within its circumference plastic, triangular, pointed, curved spears, which move only inward. Attached to the rim is a thin, hollow, rubber pocket, reinforced in a cagelike manner with heavier rubber. It can be pre-lubricated in the manner of a condom. It is inserted into the vagina by the woman wearing it by folding the pocket lengthwise and pushing it into the vaginal cavity. Upon release, the pocket expands slightly to fill the vaginal cavity. The flexible metal rim can then be pushed upward to fit into the outer end of the vaginal opening. It has two small lips, at the top and bottom of the flexible rim, which are used as grips for removal. A woman can pry either lip with a thumbnail or fingernail and draw the invention out of the vagina. It is disposable. It can be worn for more than 24 hours, as an association between wearing it and toxic shock syndrome in some women will not have been established. A physician can be consulted as to proper insertion and care. It can be made in small, medium and large sizes to accommodate different vaginas and it can be worn by women of all ages. It can be made of several types of rubber and plastic, some more flexible than others.

SUMMARY OF THE PRESENT INVENTION

The present invention relates generally to sexual protection devices for females and, more specifically, to a device for defending against and providing protection for females against rape.

A primary object of the present invention is to provide a female security and rape prevention device that will overcome the shortcomings of prior art devices.

Another object of the present invention is to provide a female security and rape prevention device which is able to retrieve evidence of rape and provide evidence for identifying a perpetrator.

An additional object of the present invention is to provide a female security and rape prevention device including pressure sensitive sensors responding to pressure applied to a vaginal wall and a microcomputer connected to the sensors for activating the device upon receipt of signals from the sensors indicating vaginal muscle contraction indicative of penile penetration.

A further object of the present invention is to provide a female security and rape prevention device which includes a double sided needle able to obtain a penile tissue sample upon pullback by the rapist.

A yet further object of the present invention is to provide a female security and rape prevention device which is able to inject a tissue irritant into the penis of a rapist upon insertion into the device.

Another object of the present invention is to provide a female security and rape prevention device that is positioned within the vaginal cavity of a female and is able to remove excess tissue irritant and retain a semen sample of the rapist.

A still further object of the present invention is to provide a female security and rape prevention device that is simple and easy to use.

An even further object of the present invention is to provide a female security and rape prevention device that is economical in cost to manufacture.

Additional objects of the present invention will appear as the description proceeds.

A female security and rape prevention device for placement within a vaginal cavity of a female to protect and minimize physical damage caused by physical sexual intercourse is disclosed by the present invention. The female security and rape prevention device includes a cylindrical housing including an outer surface, an inner surface defining a recess extending through the cylindrical housing, a first open end and a second closed end. The second closed end is inserted deeper within the vaginal cavity than the first open end and the inner surface is coated with a material able to absorb any fluid dispensed within the cylindrical housing. A plurality of pressure sensors are positioned around the outer surface for sensing contractions in walls of the vaginal cavity and at least one pressure sensor for sensing pressure caused by insertion of an object into the cylindrical cavity is positioned within the cylindrical cavity. At least one needle is positioned to extend into the inner side of the cylindrical cavity for contacting the object inserted into the cylindrical cavity and retaining a tissue sample of the object. The female security and rape prevention device also includes a microcomputer connected to the external and internal sensors for determining when an object has been inserted into the cylindrical housing and a reservoir for storing an identification dye which is released to discolor the object upon making such a determination. Furthermore, the needle is able to inject a tissue irritant into the object upon contact therewith and thus cause an irritation to form on the object. An auditory recorder may also be connected to the microcomputer and activated upon a determination that an object has been inserted therein for recording all sounds occurring during the sexual intercourse and a vibrating ring may be activated at that time to notify the user that the device has been activated.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

FIG. 3 is a perspective view in partial cross-section with parts cut away of the female security and rape prevention device of the present invention;

FIG. 4 is a side view in partial cross-section with parts cut away of the female security and rape prevention device of the present invention;

FIG. 5 is a schematic diagram illustrating electrical circuitry within the female security and rape prevention device of the present invention;

FIG. 5a is a top perspective view in partial cross-section with parts cut away of the female security and rape prevention device of the present invention illustrating optional sensor bands and a switch timer actuating cord;

FIG. 5b is a schematic diagram illustrating electrical circuitry of the female security and rape prevention device of the present invention including a vibrator ring and auditory recording device;

FIG. 6b is a side view of the female security and rape prevention device of the present invention including the second device for removal from the vaginal cavity;

Figure 1:
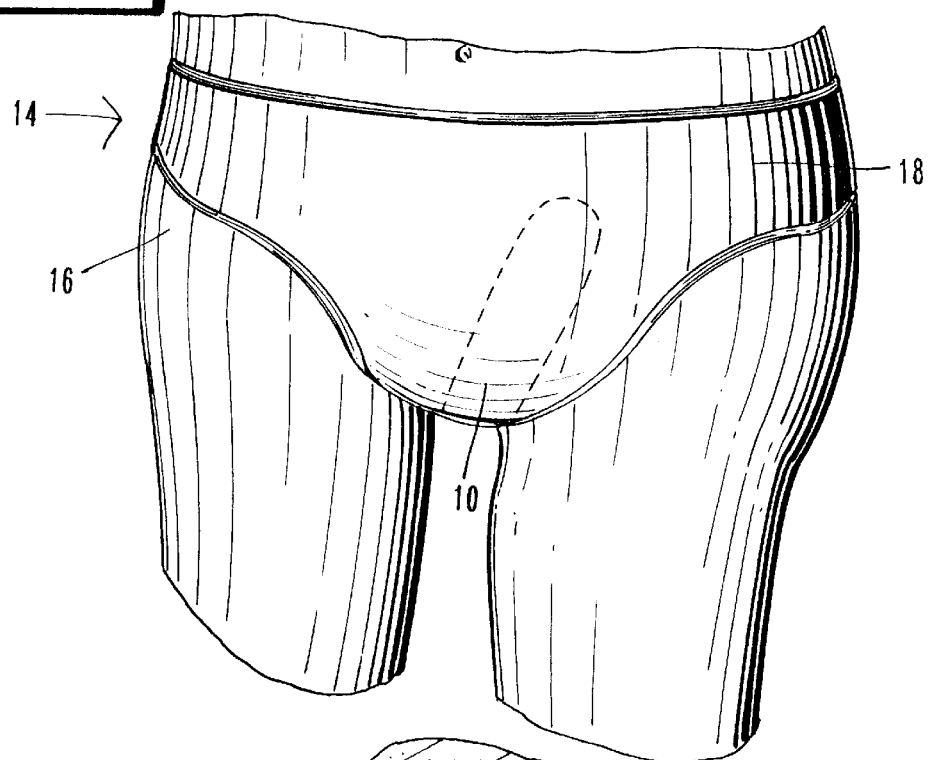
FIG. 1 is a perspective view of the female security and rape prevention device of the present invention shown in dashed lines positioned within the vaginal cavity of a woman.

FIG. 7 is a top perspective view of the female security and rape prevention device of the present invention in position inserted within a vaginal area of a female and including a surgical glue spray; and FIG. 8 is a top perspective view of the female security and rape prevention device of the present invention in position inserted within a vaginal area of a female wherein an air bag is deployed to prevent penile penetration by a potential rapist.

DESCRIPTION OF THE REFERENCED NUMERALS

Turning now descriptively to the drawings, in which similar reference characters denote similar elements throughout the several views, the Figures illustrate the female security and rape prevention device of the present invention. With regard to the reference numerals used, the following numbering is used throughout the various drawing figures.

10 midsection of female wearing the female security and rape prevention device of the present invention 12 vaginal cavity 14 female using security and rape prevention device of the present invention 16 midsection of female 18 undergarment of female 20 cylindrical housing 22 first open end of the cylindrical housing
24 second closed end of the cylindrical housing
26 frontal pressure sensor aperture
28 external surface pressure sensors
30 outer side of the cylindrical housing
32 ribs within cylindrical housing
34 inner side of the cylindrical housing
36 first needle
38 second needle
40 connection device
42 tabs
44 internal surface pressure sensors
46 jell within second closed end
48 latex bladder sealing second closed end
50 reservoir containing identification dye
52 microcomputer
54 power source
56 first group of external surface pressure sensors
58 second group of external surface pressure sensors
60 line connecting microcomputer to first group of external surface pressure sensors
62 line connecting microcomputer to second group of external surface pressure sensors
64 line connecting first internal surface pressure sensor to microcomputer
66 line connecting second internal surface pressure sensor to microcomputer
68 activation switch
70 external surface pressure sensors
72 auditory recording device
74 vibrator ring
76 foam outer covering for cylindrical housing
78 sensors molded in foam outer covering
80 central portion of connection device
82 skirt extending from central portion of connection device
84 lip extending around skirt
86 tong
88 pair of pivotal outwardly curling clips
90 handle of tong
92 arrow indicating direction of removal
94 lip around first open end of cylindrical housing
96 pair of tongs
98 pair of pivotal inwardly curling clamps
100 handle of pair of tongs
102 arrow indicating direction of removal
104 surgical glue
106 seal formed by surgical glue
108 air bag

DETAILED DESCRIPTION OF THE PREFERRED EMBODIMENT

Turning now descriptively to the drawings, in which similar reference characters denote similar elements throughout the several views, FIGS. 1 through 8 illustrate a female security and rape prevention device indicated generally by the numeral 10 and shown in dashed lines in FIG. 1.

The female security and rape prevention device 10 is positioned within a vaginal cavity 12 of a woman 14. A midsection 16 of a woman 14 is illustrated in FIG. 1. The woman 14 is wearing an undergarment 18 and the female security and rape prevention device 10 is illustrated in dashed lines in position within the vaginal cavity 12. The female security and rape prevention device 10 is positioned within the vaginal cavity 12 so as to be unobtrusive and not noticeable to persons other than the user.

Figure 2:
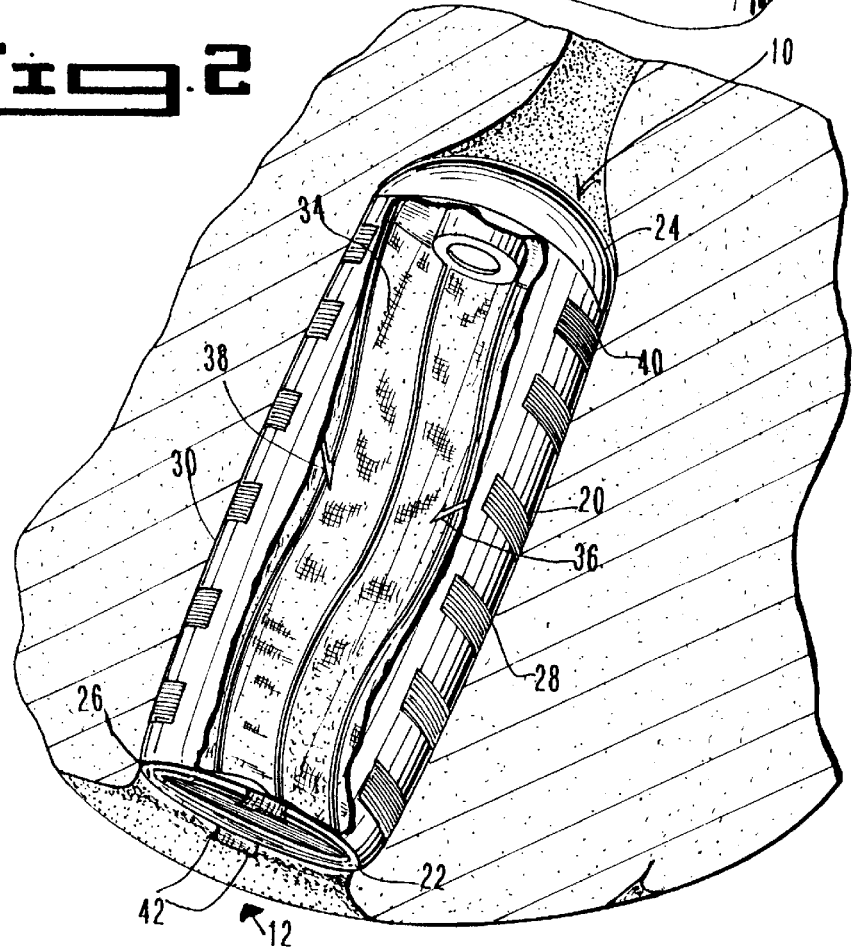
FIG. 2 is a perspective view with parts cut away of the female security and rape prevention device of the present invention.

The female security and rape prevention device 10 is sized to fit within the vaginal cavity 12 as illustrated in FIG. 2 and includes a cylindrical housing 20 having a first open end 22 and a second closed end 24. The cylindrical housing 20 is made of an absorptive flexible material able to expand and contract with the walls of the vaginal cavity 12. The first open end 22 includes a frontal pressure sensor 26 for sensing pressure caused by penile insertion and contracting upon sensing of pressure around the inserted penis. The second closed end 24 is preferably made of a flexible material and acts as a buffer to prevent trauma to the vaginal cavity 12. The preferred material for the second closed end 24 is a flexible bladder made of latex and filled with a jell like substance. However, any material which is able to close the second end of the cylindrical housing 20 while maintaining a soft flexible texture able to prevent any trauma or damage to the vaginal cavity 12 when inserted therein may be used.

A plurality of surface sensors 28 extend partially around an outer side 30 of the cylindrical housing 20 for sensing increased pressure exerted on and by the walls of the vaginal cavity 12. A plurality of ribs 32 extend along an inner side 34 of the cylindrical housing 20 for expanding and contracting the cylindrical housing 20 along with the contractions of the walls of the vaginal cavity 12 and the insertion and pullback of a penis inserted therein. Extending from the inner side 34 of the cylindrical housing 20 and into the cavity formed therein are first and second dual headed needles 36 and 38 for engaging a penis as it extends into the cylindrical housing 20 and injecting the penis with a tissue irritant. The first and second needles 36 and 38 are also able to take a tissue sample of the penis as it contacts the surface of the needles 36 and 38.

Positioned at the second end 24 on the internal side of the cylindrical housing 20 is a connection device 40 for aiding in removal of the female security and rape prevention device 10 as will be discussed in more detail hereinafter with specific reference to FIG. 6. Positioned within the connection device 40 is a microcomputer and auditory recording processor as will be discussed hereinafter with specific reference to FIGS. 4, 5 and 5b. Extending from the first end 22 of the cylindrical housing 20 are a pair of tabs 42 for use in removal of the female security and rape prevention device 10 from the vaginal cavity 12.

As is clearly illustrated in FIG. 3, a plurality of internal surface pressure sensors 44 are also positioned on the inner side 34 of the cylindrical housing 20. The internal surface pressure sensors 44 act to monitor penile advance within the female security and rape prevention device 10 and are connected to a reservoir 50 as shown in FIG. 4 containing an identification dye therein for releasing the identification dye on the penis when it is sensed by the internal surface pressure sensors 44 that the penis has advanced a certain distance into the cylindrical housing 20. The first and second needles 36 and 38 extend from the internal surface pressure sensors 44 and help monitor penile advancement into the cylindrical housing 20. The first and second needles 36 and 38 trigger the internal surface pressure sensors 44 to release the identification dye from the reservoir 50 when they are contacted by a penis. A cut away portion of this figure also shows the jell substance 46 within the bladder 48 of the second closed end 24. The positioning of the internal surface pressure sensors 44, the reservoir 50 for retaining the identification dye and the first and second needles 36 and 38 within the cylindrical housing 20 is clearly illustrated in FIG. 4.

A schematic diagram illustrating electrical components contained within the cylindrical housing 20 of the present invention and their interconnection is shown in FIG. 5. As can be seen in this figure the connection device 40 houses a microcomputer 52 and a power source 54. The plurality of external surface sensors 28 are divided into first and second groups of sensors 56 and 58, the first group 56 partially extending around a first half of the outer side 30 of the cylindrical housing 20 and the second group 58 partially extending around a second half of the outer side 30 of the cylindrical housing 20. The microcomputer 52 is connected to the first group of external surface sensors 56 through a first connection wire 60 and to the second group of external surface sensors 56 through a second connection wire 62. The microcomputer 52 is also connected to the internal surface pressure sensors 44 by third and fourth connection wires 64 and 66. A switch 68 is also connected to the microcomputer 52 for manually activating the female security and rape prevention device 10 when it is determined by the user that a rape or unwanted sexual contact is eminent. The manual switch 68 allows for selective activation of the female security and rape prevention device 10 and thus will prolong the life of the power source 54 as it will not be drained constantly but only during times of need.

Figure 5C:
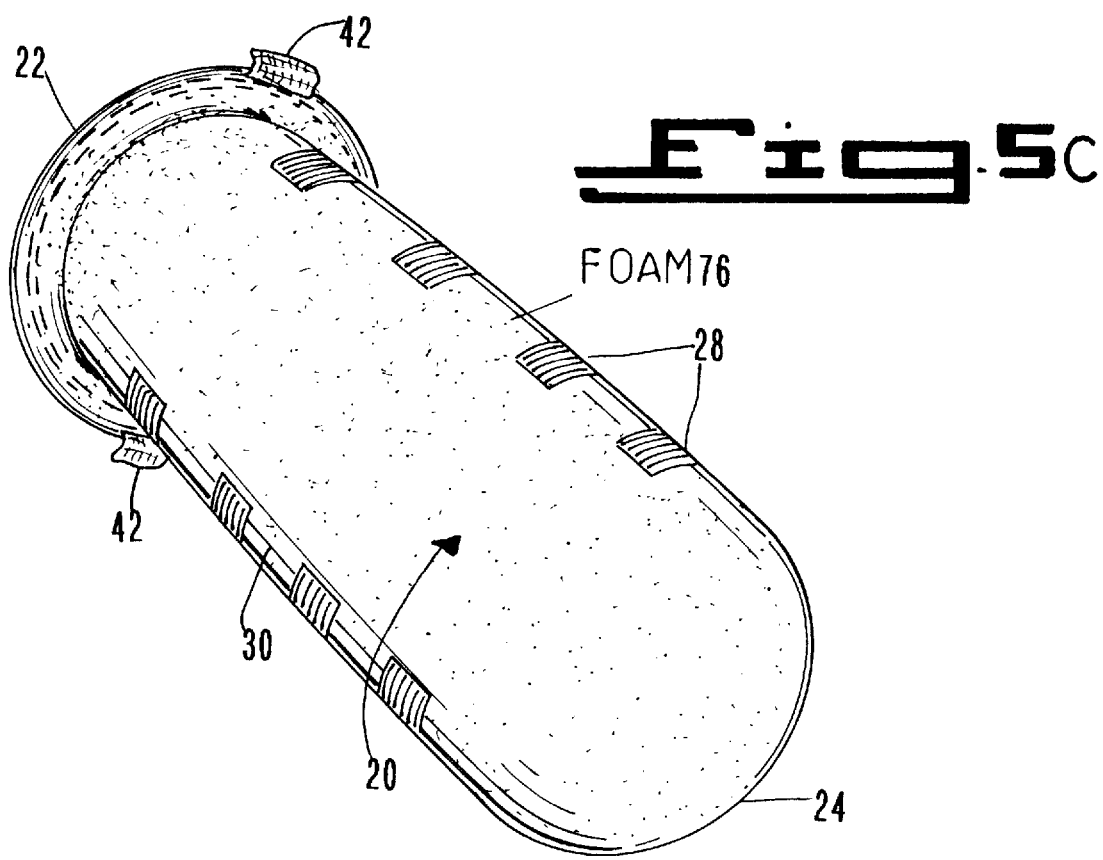
FIG. 5c is a top perspective view of the female security and rape prevention device of the present invention including a foam outer layer.
Figure 5D:
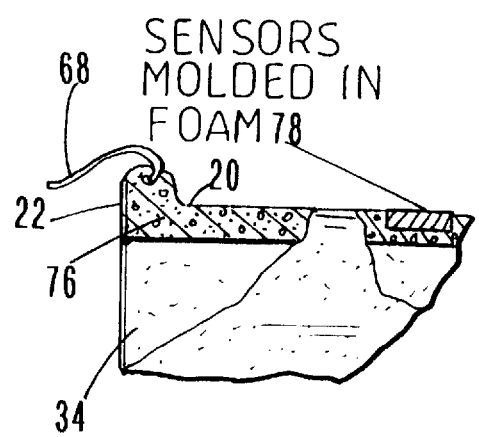
FIG. 5d is an exploded view of a portion of an outer layer of the female security and rape prevention device of the present invention illustrated in FIG. 5c including sensors molded in the foam outer layer.

FIG. 5a illustrates an optional form for the external pressure sensors 28. Instead of having first and second groups 56 and 58 of external pressure sensors 28, a plurality of circular external pressure sensors 70 may be spacedly positioned along the length of the outer side 30 of the cylindrical housing 20, each extending around the entire circumference of the cylindrical housing 20. An additional auditory recording device 72 and a vibrator ring 74 are shown in FIG. 5b connected to the microcomputer 52. The auditory recording device 72 is activated by the microcomputer 52 upon a determination that a rape is occurring and produces an auditory recording of the incident to provide further proof of the occurrence of a rape. The vibrator ring 74 is also activated by the microcomputer 52 upon a determination that a rape is occurring and causes the female security and rape prevention device 10 to vibrate thus alerting the user that it is activated. The determination by the microcomputer 52 that a rape is occurring is based upon an analysis of the signals received from both the external pressure sensors 28 and internal sensors 44 via the respective connection wires. FIG. 5c illustrates the use of a foam coating 76 for the external surface 30 of the cylindrical housing 20. Alternatively, the material coating the outer side 30 of the cylindrical housing 20 may be a jell, soft plastic or any other soft, pliable, conductive material which will not cause discomfort when inserted into the vaginal cavity 12. Furthermore, this material could be warmed by the body temperature of the user and thus be further concealed from a would-be attacker. An alternate way of connecting the external surface pressure sensors 78 is to embed or mold them in the foam cover layer 76 as depicted in FIG. 5d. This provides the female security and rape prevention device 10 with a smoother outer surface and thus is more comfortable for the user.

Figure 6:
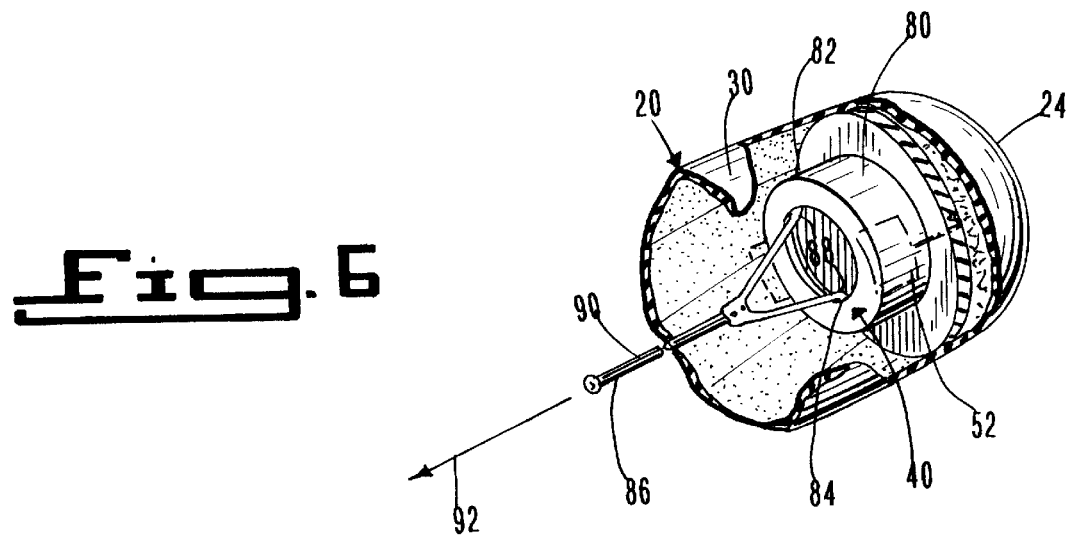
FIG. 6 is a top perspective view in partial cross-section with parts cut away of a top portion of the female security and rape prevention device of the present invention including a first device for removal from the vaginal cavity.

The connection device 40 is illustrated in FIG. 6 and includes a central portion 80 housing the microcomputer 52 along with the power supply and auditory recording device 72 as shown in FIG. 5b. Depending from the central portion 80 is a skirt 82 including a lip 84 extending therearound. The combination of the skirt 82 and lip 84 create a recess above the central portion 80. In order to remove the female security and rape prevention device 10 from its implanted position in the vaginal cavity 12, a tong 86 including a pair of pivotal outwardly curling clips 88 extending therefrom is inserted into and through the cylindrical housing 20 to engage an underside of the lip 84. Once the pair of pivotal outwardly curling clips 88 engage the lip 84 the female security and rape prevention device 10 may be easily removed from within the vaginal cavity by pulling a handle 90 of the tong 86 in a direction away from the vaginal cavity 12 as is indicated by the arrow labeled 92.

Figure 6A:
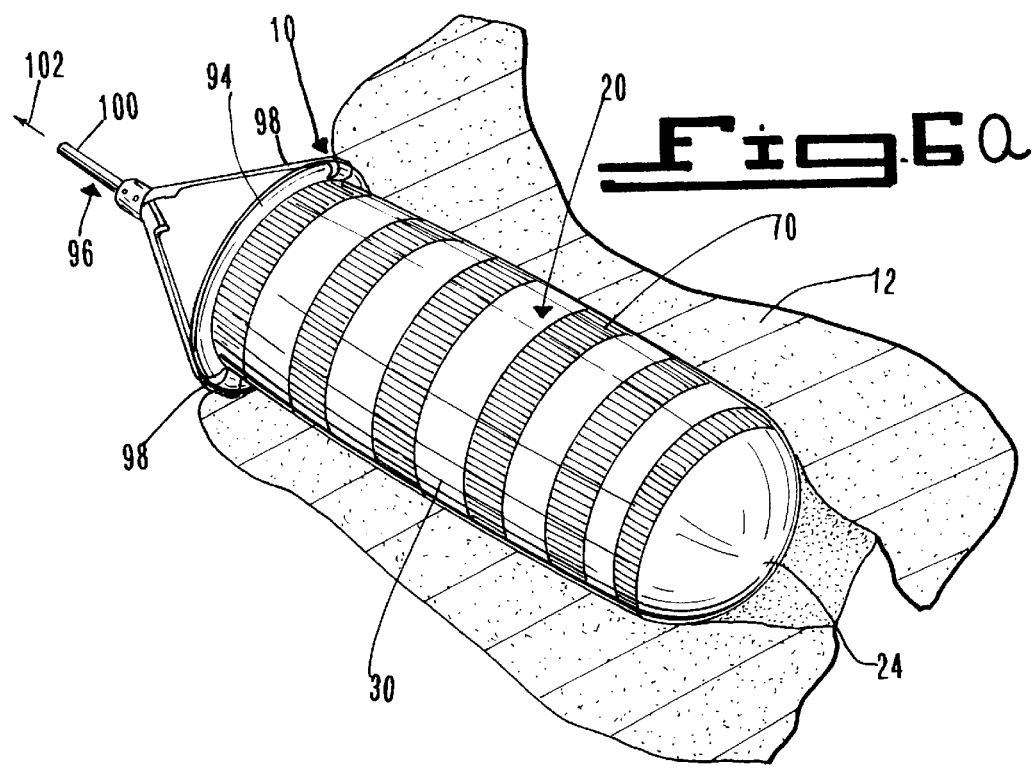
FIG. 6a is a top perspective view of the female security and rape prevention device of the present invention including a second device for removal from the vaginal cavity.

An alternative device for removing the female security and rape prevention device 10 is illustrated in FIGS. 6a and 6b. In this embodiment a lip 94 extends around the first open end 22 of the cylindrical housing 20. This lip 94 may be used instead of the pair of tabs 42 described above with reference to FIGS. 2 and 3. However, the removal of the female security and rape prevention device 10 is performed in the same manner when either is used. The use of the lip 94 or the pair of protrusions 42 is simply a design choice. In order to remove the device a pair of tongs 96 including a pair of pivotal inwardly curling clamps 98 connected to a handle portion 100 are inserted into the vaginal cavity 12. The pair of pivotal inwardly curling clamps 98 are caused to engage the lip 94 and then a force is exerted on the handle portion 100 in the direction of the arrow labeled 102 out of the vaginal cavity 12 until the female security and rape prevention device 10 is removed therefrom. Alternatively, the user may remove the female security and rape prevention device 10 without the pair of tongs 96 by grasping the pair of tabs 42 or lip 94 and exerting a force in the direction of the arrow 102 out of the vaginal cavity 12.

Also contained within the inner side 34 of the cylindrical housing 20 is a surgical glue 104 as illustrated in FIG. 7. This surgical glue 104 is released upon pull back of the penis by the rapist and acts to form a seal 106 and close the front open end 22 of the cylindrical housing 20 preventing any further penile penetration. Alternatively, a small air bag 108 as illustrated in FIG. 8 may be retained within the cylindrical housing 20 and deployed to prevent further penile penetration. The air bag 108 is deployed to seal the first open end 22 of the cylindrical housing 20 upon a determination by the microcomputer 52 that a rape or some object has been inserted into the cylindrical housing 20 is occurring.

The operation of the device will now be described with reference to the figures. In operation, the female security and rape prevention device 10 is inserted within the vaginal cavity 12 of a user by placing the female security and rape prevention device 10 at the entrance to the vaginal cavity 12. A force is then exerted on either the pair of tabs 42 or the lips 94 towards the vaginal cavity 12 until the female security and rape prevention device 10 is fully inserted therein.

Due to the soft pliable nature of the material of which the female security and rape prevention device 10 is composed the user should feet a minimal amount of discomfort once the device is inserted. If the user feels a large amount of discomfort the device should either be adjusted within the vaginal cavity 12 until the discomfort is gone or removed, checked to make sure it is working properly, e.g. that the tissue irritant is not leaking, there are no sharp ends sticking through the outer surface or any other items which might be the cause of discomfort, and reinserted into the vaginal cavity 12.

While in the vaginal cavity 12 the female security and rape prevention device 10 should not prevent the user from performing any of her normal daily activities and thus the user can go on and perform all normal activities she would otherwise perform. If the user is presented with a rape situation, she may then activate the device using the switch 68 and thus the device should now be functional. Upon activation of the switch 68 the vibrator ring 74 should vibrate to alert the user that the device is operational. If there is no switch to activate, the device will automatically activate when penile penetration into the cylindrical housing is sensed by the internal sensors 44 and contractions of the vaginal wall are sensed by the external surface pressure sensors 28 or 70. These sensors send signals to the microcomputer 52 which analyze the signals to determine if a rape situation exists. If it is determined that a rape situation exists, the microcomputer 52 will activate the vibrator ring 74 to vibrate and thus alert the user that the female security and rape prevention device 10 has been activated.

Upon activation of the device, the auditory recording device 72 is activated to record any sounds produced during the rape and the identification dye is caused to be released from the reservoir 50 by the internal surface pressure sensors 44. The release of the identification dye causes the dye to contact the penis which has penetrated into the cylindrical housing 20 and cause a discoloration to the outer skin of the penis for use in later proving sexual intercourse. Any of the identification dye which is not removed with the penis is absorbed by the foam material covering the inner side 34 of the cylindrical housing 20.

When a penis is inserted into the cylindrical housing 20 the frontal pressure sensitive aperture 26 and the ribs 32 extending along the inner side 34 of the cylindrical housing 20 are caused to expand and contract with the insertion and removal forces caused by insertion and pullback of the penis. As the penis is inserted it is also caused to contact the first and second needles 36 and 38. When these needles 36 and 38 are contacted by the penis a pressure is applied thereto and the needles 36 and 38 cause the internal surface pressure sensors 44 to send a signal indicating an object has been inserted into the cylindrical housing 20 to the microcomputer 52. The needles 36 and 38 also inject a tissue irritant into the penis causing an irritation of the skin on the penis to form. Any additional tissue irritant dispensed within the cylindrical housing 20 is absorbed by the foam material covering the inner side 34 of the cylindrical housing 20. Furthermore, the first and second needles 36 and 38 include a double edged head which acts to retrieve a tissue sample of the penis inserted into the cylindrical housing for future identification purposes.

If a surgical glue 104 as illustrated in FIG. 7 is contained within the cylindrical housing 20 it is caused to be dispensed upon pullback of the penis and forms a seal 106 within the cylindrical housing 20 preventing further insertion of a penis and thus preventing any further rape. If an air bag 108 as illustrated in FIG. 8 is contained within the cylindrical housing 20 it is deployed upon pullback of the penis and seals the open front end 22 of the cylindrical housing 20 preventing further insertion of the penis. If neither the surgical glue 104 nor the air bag 108 are contained within the cylindrical housing 20 repeated insertion and pullback of the penis is permitted and any semen deposited within the cylindrical housing is absorbed by the foam material covering the inner side 34 of the cylindrical housing 20. The female security and rape prevention device 10 thus blocks the cervix of the user and also protects the vaginal surface from bacterial infection, viral infection and semen entry.

From the above description it can be seen that the female security and rape prevention device of the present invention is able to overcome the shortcomings of prior art devices by providing a female security and rape prevention device which is able to retrieve evidence of rape and provide evidence for identifying a perpetrator. The female security and rape prevention device includes pressure sensitive sensors responding to pressure applied to a vaginal wall and a microcomputer connected to the sensors for activating the device upon receipt of signals from the sensors indicating vaginal muscle contraction indicative of penile penetration and a double sided needle able to obtain a penile tissue sample upon pullback by the rapist. The female security and rape prevention device is also able to inject a tissue irritant into the penis of a rapist upon insertion into the device is positioned within the vaginal cavity of a female and remove excess tissue irritant and retain a semen sample of the rapist. Furthermore, the female security and rape prevention device of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A female security device connected to a power supply for placement within a vaginal cavity of a female to protect and minimize physical damage caused by sexual intercourse, said female security device comprising:

a) a cylindrical housing including an outer surface, an inner surface, a first open end and a second closed end, said second closed end being inserted deeper within the vaginal cavity than said first open end and said inner surface being able to absorb any fluid dispensed within said cylindrical cavity;

b) a plurality of pressure sensors positioned around said outer surface for sensing contractions in walls of the vaginal cavity;

c) means for sensing pressure caused by insertion of an object into said cylindrical cavity positioned within said cylindrical cavity; and d) at least one needle extending into said inner side of said cylindrical cavity for contacting the object inserted into said cylindrical cavity and retaining a tissue sample of said object.

2. The female security device as recited in claim 1, further comprising a microcomputer connected to said plurality of pressure sensors and said means for sensing pressure for determining when the object has been inserted into said cylindrical housing.

3. The female security device as recited in claim 2, further comprising a reservoir containing an identification dye connected to dispense said dye on the object when said microcomputer determines the object has been inserted into said cylindrical housing.

4. The female security device as recited in claim 2, further comprising a vibrating ring connected to said microcomputer for vibrating when said microcomputer determines the object has been inserted into said cylindrical housing and thereby alerting the user that the device has been activated.

5. The female security and rape prevention device as recited in claim 2, further comprising an auditory recording device connected to said microcomputer for recording all auditory sounds when said microcomputer determines the object has been inserted into said cylindrical housing.

6. The female security and rape prevention device as recited in claim 2, further comprising a surgical glue contained within said cylindrical housing being dispensed to form a seal closing said first open end upon a determination by said microcomputer that the object has been pulled back out of the vaginal cavity.

7. The female security and rape prevention device as recited in claim 2, further comprising an air bag contained within said cylindrical housing being deployed to close said first open end upon a determination by said microcomputer that the object has been pulled back out of the vaginal cavity.

8. The female security device as recited in claim 1, wherein the power supply is located within said cylindrical housing and further comprising a switch for manually connecting the power supply to said microcomputer and thereby activating the device.

9. The female security and rape prevention device as recited in claim 1, further comprising a connection device positioned within said cylindrical housing and a clamp means for removeably engaging said connection device for removing said device from within the vaginal cavity.

10. The female security and rape prevention device as recited in claim 1, further comprising at least one tab extending from said first open end of said cylindrical housing and a clamp means for removably engaging said at least one tab to remove said device from the vaginal cavity.

11. The female security and rape prevention device as recited in claim 1, further comprising a ring extending around said first open end of said cylindrical housing and a clamp means for removably engaging said ring to remove said device from the vaginal cavity.

12. The female security and rape prevention device as recited in claim 1, further comprising a pressure sensitive device connected to said first open end of said cylindrical housing for expanding and contracting said first open end with insertion into and pullback from the cylindrical housing of the object.

13. The female security and rape prevention device as recited in claim 1, further comprising a plurality of ribs extending along said inner surface of said cylindrical housing for expanding and contracting said cylindrical housing with insertion into and pullback from the cylindrical housing of the object.

14. The female security and rape prevention device as recited in claim 1, wherein said plurality of pressure sensors each extend around the circumference of said outer side of said cylindrical housing.

15. The female security and rape prevention device as recited in claim 14, wherein said plurality of pressure sensors are embedded within said outer side of said cylindrical housing.

16. The female security and rape prevention device as recited in claim 1, wherein each of said plurality of pressure sensors extend partially around said outer side of said cylindrical housing.

17. The female security and rape prevention device as recited in claim 16, wherein said plurality of pressure sensors are embedded within said outer side of said cylindrical housing.

18. The female security and rape prevention device as recited in claim 16, wherein said soft flexible material forming said second closed end is filled with a jell-like substance.

19. The female security and rape prevention device as recited in claim 1, wherein said second closed end is formed of a soft flexible material.

* * * * *